United States Patent [19]

Harjunmaa et al.

[11] Patent Number: 5,112,124
[45] Date of Patent: May 12, 1992

[54] METHOD AND APPARATUS FOR MEASURING THE CONCENTRATION OF ABSORBING SUBSTANCES

[75] Inventors: Hannu Harjunmaa, Vessy, Switzerland; Robert A. Peura, Princeton; Yitzhak Mendelson, Worcester, both of Mass.

[73] Assignee: Worcester Polytechnic Institute, Worcester, Mass.

[21] Appl. No.: 511,341

[22] Filed: Apr. 19, 1990

[51] Int. Cl.⁵ .................... G01N 21/59; G01N 33/49
[52] U.S. Cl. .................................... 356/39; 128/633
[58] Field of Search ............... 356/39, 41; 250/339, 250/341; 128/633

[56] References Cited

U.S. PATENT DOCUMENTS

| | | |
|---|---|---|
| 1,758,088 | 5/1930 | Schmick . |
| 2,721,942 | 10/1955 | Friel et al. . |
| 3,463,142 | 8/1969 | Harte . |
| 3,638,640 | 2/1972 | Shaw . |
| 3,799,672 | 3/1974 | Vurek ........................ 356/41 |
| 3,926,527 | 12/1975 | Pembrook et al. . |
| 3,958,560 | 5/1976 | March . |
| 3,963,019 | 6/1976 | Quandt . |
| 4,029,085 | 6/1977 | DeWitt et al. ................... 128/2 R |
| 4,033,330 | 7/1977 | Willis et al. . |
| 4,169,676 | 10/1979 | Kaiser . |
| 4,266,554 | 5/1981 | Hamaguri . |
| 4,267,844 | 5/1981 | Yamanishi . |
| 4,306,877 | 12/1981 | Lübbers . |
| 4,321,930 | 3/1982 | Jöbsis et al. . |
| 4,380,240 | 4/1983 | Jöbsis et al. . |
| 4,398,541 | 8/1983 | Pugliese . |
| 4,427,889 | 1/1984 | Müller . |
| 4,485,820 | 12/1984 | Flower . |
| 4,513,751 | 4/1985 | Abe et al. . |
| 4,570,638 | 2/1986 | Stoddart et al. . |
| 4,586,513 | 5/1986 | Hamaguri . |
| 4,603,700 | 8/1986 | Nichols et al. . |
| 4,621,643 | 11/1986 | New, Jr. et al. . |
| 4,653,498 | 3/1987 | New, Jr. et al. . |
| 4,655,225 | 4/1987 | Dähne et al. ...................... 250/339 |
| 4,704,029 | 11/1987 | Van Heuvelan . |
| 4,725,147 | 2/1988 | Stoddart . |
| 4,750,496 | 6/1988 | Reinhart et al. . |
| 4,759,369 | 7/1988 | Taylor . |
| 4,768,516 | 9/1988 | Stoddart et al. . |
| 4,796,636 | 1/1989 | Branstetter et al. . |
| 4,805,623 | 2/1989 | Jöbsis . |
| 4,817,623 | 4/1989 | Stoddart et al. . |
| 4,832,484 | 5/1989 | Aoyagi et al. ..................... 356/41 |
| 4,863,265 | 9/1989 | Flower et al. ..................... 356/41 |
| 4,882,492 | 11/1989 | Schlager . |
| 5,028,787 | 7/1991 | Rosenthal et al. ................ 250/341 |

FOREIGN PATENT DOCUMENTS

| | | |
|---|---|---|
| 0074428 | 3/1983 | Fed. Rep. of Germany . |
| 0160768 | 4/1984 | PCT Int'l Appl. . |
| WO90/07905 | 1/1990 | PCT Int'l Appl. . |

OTHER PUBLICATIONS

"Blood Glucose Sensors: An Overview" by R. A. Peura and Y. Mendelson—1984, pp. 63–68.

Primary Examiner—Richard A. Rosenberger
Attorney, Agent, or Firm—Hamilton, Brook, Smith & Reynolds

[57] ABSTRACT

A non-invasive system for measuring the concentration of an analyte in an absorbing matrix is described. The system directs a beam of radiation at the matrix. The beam consists of a series of successive alternate pulses of electro-magnetic radiation, one of which is highly absorbed by the analyte and the other of which is non-absorbed. The transmitted or reflected beam is optically detected and an electrical signal proportional to beam intensity is used to adjust the beam intensity and as a measure of analyte concentration.

18 Claims, 3 Drawing Sheets

METHOD AND APPARATUS FOR MEASURING THE CONCENTRATION OF ABSORBING SUBSTANCES

BACKGROUND OF THE INVENTION

This invention relates to the non-invasive measurement of the concentration of substances that absorb electromagnetic radiation, such as light or infrared radiation, in absorbing and turbid matrices. In particular, the invention is directed to substances, such as glucose, found in the blood of absorbing and turbid matrices, such as human or animal body tissue.

Numerous techniques have been proposed for the determination of glucose by non-invasive optical monitoring methods. (See "Blood Glucose Sensors: An Overview", by Peura, R. A. and Mendelson, Y., Proceedings of the IEEE/NSF Symposium on Biosensors, Los Angeles, Calif., 1984.) Many of the proposed methods rely on transmissive and diffuse reflective absorption measurements using infrared radiation.

The infrared measurement methods known in the art are not well adapted to the problem of quantifying an analyte dissolved in a strongly absorbing solvent. The known methods include separate or directly alternating measurements using radiations at a "glucose" wavelength and at a "reference" wavelength, where glucose does not absorb, as well as differential wavelength modulation about a glucose absorption band (C. Dahne, D. Gross, European Patent 0 160 768 and references therein). In the known methods, the signal is easily lost into the strong background presented by the water in tissues and in the capillary blood flow. The normal concentration range of glucose in blood for male adults is 4 to 6 mmol/l (70 to 110 mg/dl).

A need still exists, therefore, for a non-invasive method and apparatus having sufficient long-term sensitivity to accurately measure the concentration of light absorbing substances in absorbing and turbid matrices found in the human or animal body.

SUMMARY OF THE INVENTION

The present invention comprises a system which periodically or continuously directs two beams of electromagnetic radiation of different wavelengths $\lambda_1$ and $\lambda_2$, respectively, at a radiation absorbing body. The radiation at one wavelength $\lambda_1$ is alternated at equal successive intervals in time with radiation at the other wavelength $\lambda_2$.

One of the wavelengths, say $\lambda_1$, is chosen to be highly absorbent by the analyte to be measured, while the other, $\lambda_2$, is selected to be substantially non-absorbed by the analyte. In this manner, a single beam is formed of a series of successive alternate pulses of equal duration and amplitude of radiation $\lambda_1$ and $\lambda_2$. The transmissive/reflective beam is optically detected and an electrical signal is generated proportional to the detected beam intensity. With no analyte present, the system is calibrated so that the intensity of the detected beam is a constant D.C. signal during the pulse periods.

The variation of the detected signal when the analyte is present is integrated over time to produce a control signal. This control signal is used to constantly adjust the intensity of one of the laser beams in a direction which tends to bring the detected signal to zero or null. The control signal is also a measure of the analyte concentration and is calibrated against a reference voltage and displayed as an analyte concentration value.

An important difference between the present method and those known in the prior art is that, in contrast to the known methods, the method of this invention forms the difference of the signals obtained at an analyte wavelength $\lambda_1$ (where the analyte absorbs), and a reference wavelength $\lambda_2$ (where the analyte essentially does not absorb) directly at the optical level (i.e., by optical means), instead of comparing electronically the two signals at the analog or digital level (i.e., by electronic circuitry means). The difference of the intensity signals at $\lambda_1$ and $\lambda_2$ is used in an optical null arrangement which, as its output, gives a control signal proportional to the concentration of the analyte.

The two wavelengths $\lambda_1$ and $\lambda_2$ are selected so the radiation has exactly the same degree of matrix extinction at these wavelengths. Note: The matrix extinction is the sum of the absorption and scattering experienced by the beam in a matrix sample without the analyte. With the method of this invention, one can detect lower glucose concentrations in human tissue than with the currently known methods.

DETAILED DESCRIPTION OF THE DRAWINGS

Figure 1:
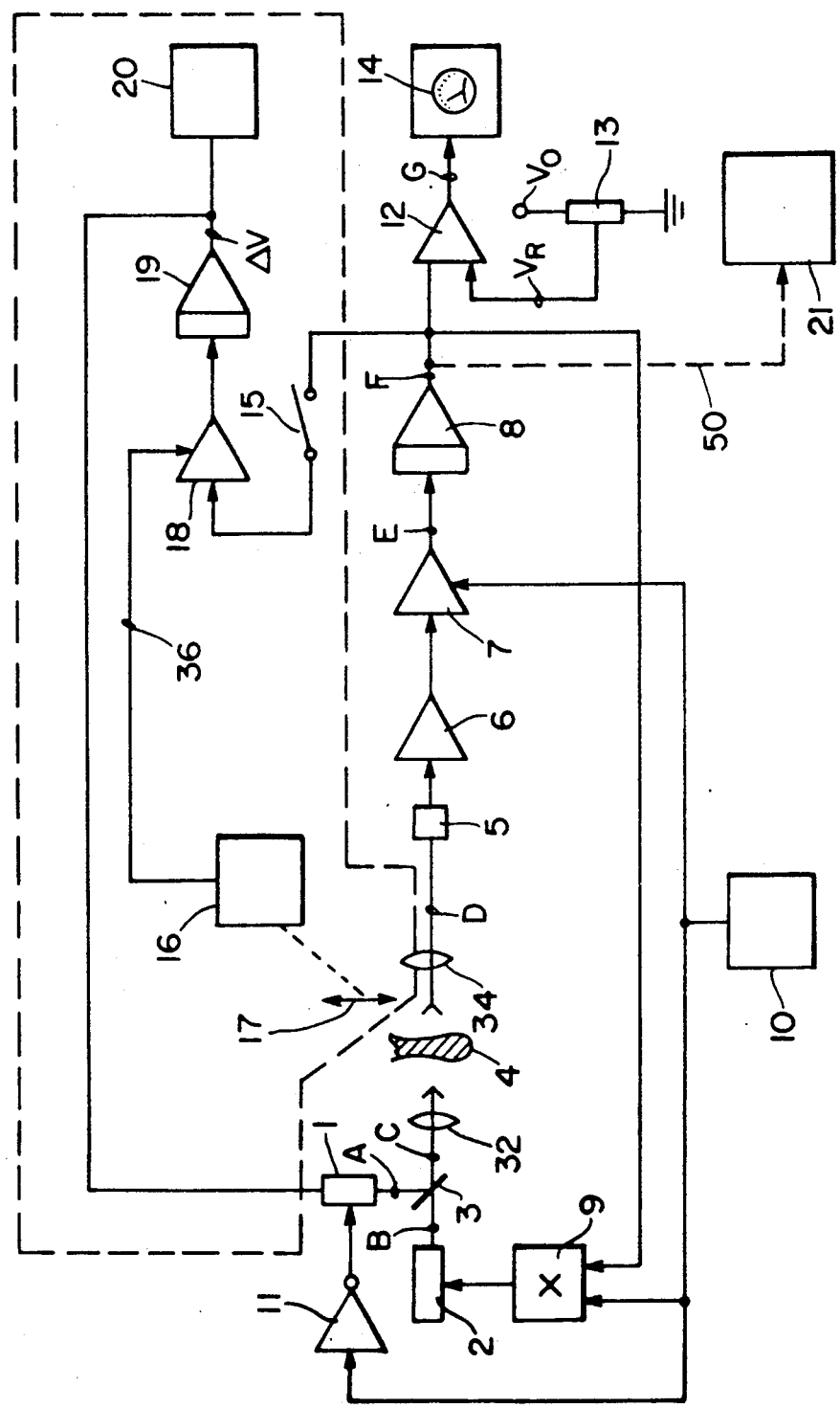

FIG. 1 is a block diagram of the system of the invention.

Figure 2:
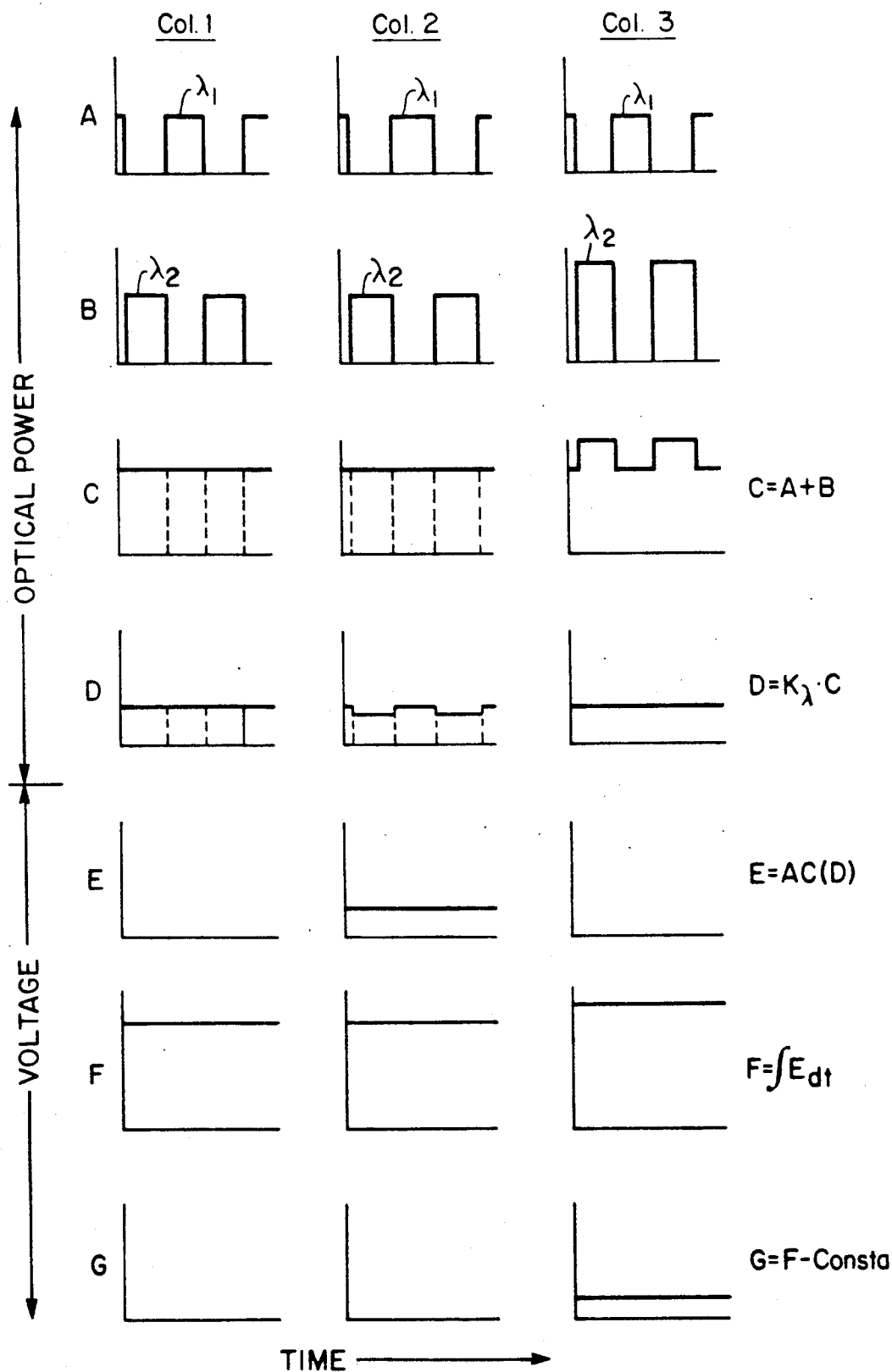

FIG. 2 is a timing diagram showing Rows A-G of waveforms at different locations in the block diagram of FIG. 1. The three columns show the waveforms under different analyte conditions, i.e., Column 1 is the calibrated condition with no analyte present in the sample matrix, Column 2 the transient condition after introduction of the analyte into the sample matrix and Column 3 with analyte after steady state is obtained.

Figure 3:
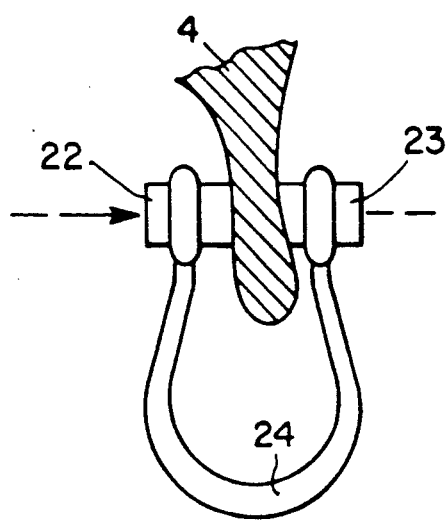

FIG. 3 is a schematic representation of an optical device for use in maintaining the optical probe in fixed position on the subject of measurement.

DETAILED DESCRIPTION OF THE INVENTION

The invention will now be described in connection with the drawings.

The invention is described as applied to the special case of glucose measurement in human tissue using near-infrared radiation. This should in no way detract from the general applicability of the invention to measure the concentration of any species that absorbs electromagnetic radiation, especially in strongly absorbing and turbid matrices.

A. GENERAL OPERATION

In the method of this invention, the measurement is made by combining into a single beam (curve C), the alternate pulses curve A and curve B defined as "half-periods" of radiation at two wavelengths $\lambda_1$ and $\lambda_2$. The single beam is directed against the sample 4, i.e., an ear lobe, thus providing a response beam (curve D) to be detected by a detector 5. With no analyte present, the optical intensity should be constant, as shown in curve D, row 1. The electrical response generated in the detector 5 by the constant intensity $\lambda_1$ and $\lambda_2$ half-period response beam is calibrated to be zero, or null (curve E row 1). When there is a nonzero concentration of the analyte, the intensity of the beam is no longer constant. The intensity of one of the half-periods changes with respect to the other, as shown in curve D row 2. This change is detected by detector 5 and the amplitude of the alternating-current (AC) signal given by the detector 5 is representative of the analyte concentration (curve E row 2). This signal is not used directly to quantify the analyte concentration, but is used, instead, in an optical null arrangement to change the relative intensity of the two half-periods. The AC signal is amplified and rectified in the lock-in amplifier 7. The resulting DC signal is integrated in integrator 8 to produce a control signal (curve F row 3). The value of the control signal needed to restore the signal from the detector 5 to zero (curve E row 3) is used as the indicator of the analyte concentration.

The measurement geometry may be either direct transmission, transflection or attenuated total reflection. Direct transmission is shown herein by way of example.

B. THEORY

The principles governing the method of the present invention are briefly outlined below with the assumption that the Beer-Lambert law, $P = P_o e^{-kx}$ is valid.

In the above relation, $P_o$ is the power of the incident collimated beam falling on the sample, k is the absorption coefficient (usually in 1/cm) and x is the length (in cm) of the sample in which interaction occurs. To simplify the equations, only essential quantities are retained and the signal is considered radiative only; scattering can be included in k, and, if its contribution is desired explicitly, it is a straightforward operation to replace k by the sum of absorption and scattering effects.

In view of the above, the powers collected at wavelengths $\lambda_1$ and $\lambda_2$ are $P_{\lambda 1} = P_{01} e^{-k1x}$ and $P_{\lambda 2} = P_{02} e^{-k2x}$, respectively.

Since provision is made that the absorption of the background is the same at $\lambda_1$ and $\lambda_2$, the difference $$S = \Delta P = P_{\lambda 1} - P_{\lambda 2} = 0$$

if no analyte is present. This difference is hereafter called the error signal. The electrical signal produced in the detector is assumed to be proportional to the optical power.

When analyte is present, it absorbs at one of the wavelengths, but not at the other, which means that for the first wavelength, say $\lambda_2$, the absorption coefficient has changed by, say, $\Delta k$. Hence now, $$S \neq 0 = P_0[e^{-(k-\Delta k)x} - e^{-kx}] \text{ or}$$
$$= P_0 e^{-kx}[e^{\Delta kx} - 1].$$

Now for $\Delta k$ small, i.e., <0.1, the known approximation $e^{\Delta kx} = 1 + \Delta kx$ holds; so $S = P_0 \Delta kx \, e^{-kx}$, i.e., the error signal is proportional to $\Delta k$, that is, to the analyte concentration. Also, it can be seen that the error signal has a maximum with respect to path length, for a given analyte concentration. This maximum can be obtained by taking the derivative of the above equation. It occurs at the path length of 1/k.

When the concentration of analyte is nonzero, an error signal is generated, but the system strives to keep it at zero by changing the intensity of one component wavelength;

$$P_{02} = (1 + f) P_{01}.$$

Here, f is the relative change in the intensity at $\lambda_2$ with respect to the equilibrium state.

$$S = P_{01} e^{-k1x} - P_{02} e^{-k2x} = 0$$

$$P_{01} e^{-k1x} - (1+f) P_{01} e^{-k2x} = 0$$

$$e^{-k1x} = (1+f) e^{-k2x}$$

$$1 + f = e^{\Delta kx}.$$

If $\Delta kx$ is small, which is to be expected, the approximation $e^{\Delta kx} = 1 + \Delta kx$ is valid, which leads to $$f = \Delta kx,$$

or, the relative deviation from equilibrium intensity is proportional to analyte concentration and to path length.

If there is some analyte absorption at the reference wavelength, the signal diminishes in proportion to the difference of the analyte absorptions at the analyte wavelength and the reference wavelength.

In order to account correctly for scattering, the wavelength choice must be made on the basis of the sum spectrum of absorption and scattering in the sample matrix (that is, extinction spectrum), with due consideration to the measuring geometry, which affects the relative importance of scattering.

Table 1, below, indicates a few wavelengths at which glucose absorbs which can be used to practice the invention in combination with the background absorption values on the same line of the Table. Water absorption coefficients at the indicated wavelengths are also in the Table.

TABLE I

| Wavelength in (μm) | Glucose Absorption (μm) | Background Absorption (μm) | $kH_2O$ (l/cm) |
|---|---|---|---|
| 1.57 | 1.75 (gl)*, | 1.38 (st)* | 9 |
| 1.77 | 1.55 (gl), | 1.39 (st) | 7 |
| 2.10 | 2.29 (gl). | 1.87 (st), 1.48 (pk)* | 30 |
| 2.17 | 1.86 (st) | 1.49 (st), 1.41 (st) | 25 |
| 2.27 | 2.15 (gl) | 1.86 (st), 1.48 (pk), 1.40 (st) | 30 | where: *st = steep; pk = peaking; gl = glucose absorption.

For fine tuning the wavelengths, one keeps a member of the pair constant while the other is adjusted. Preferably, the glucose wavelength is kept constant in order to have a constant sensitivity for glucose. The reference wavelength is preferably situated on a moderate or shallow slope of the water absorption spectrum: with a steep slope, accurate control is more difficult. In Table 1, some reference wavelengths are situated on a steep slope; others are at or near a peak; some reference wavelengths have glucose absorption.

The fine tuning can be achieved automatically, as will be described in the alternate embodiment, shown i dotted lines in FIG. 1.

C. PREFERRED EMBODIMENT

The following example illustrates the invention with reference to the annexed drawings. This invention can be carried out using many other embodiments not specifically exemplified here but which should not be excluded from protection.

Because of the strength of glucose absorption at 2.1 μm, the present embodiment has been devised for the wavelength pair 2.10/1.48 μm. This wavelengths selection is only one example, no other suitable wavelength pairs being excluded from the scope of this application.

Referring to FIGS. 1 and 2, the radiation source of this example consists of two pulsed lasers 1,2 operating at the wavelengths $\lambda_1$ and $\lambda_2$, respectively. In the timing diagram of FIG. 2, the optical intensity of these beams and the resulting detected voltages at various points in the system are plotted versus time for different conditions. That is, Column 1 shows the various waveforms for a calibrated system in which no analyte is present in the matrix, Column 2 shows the transient condition after introduction of analyte into the sample matrix, and Column 3 shows the steady state condition with analyte present in the sample matrix. The following is a summary of the timing diagram waveforms:

A. Relative optical power in the constituent beam marked A.
B. Relative optical power in the constituent beam marked B. which is modulated in antiphase to A. The on-value of this power is adjustable and proportional to the signal F.
C. Relative optical power in the combined beam before the sample. In a calibrated system without sample, this has no AC component.
D. Relative optical power after the sample. The system seeks to keep the AC component of D to zero.
E. Lock-in amplifier 7 output, proportional to the AC component of D. This is the error signal for the servo loop. The system seeks to keep E to zero.
F. Integrated error signal equals the intensity control voltage for one of the constituent beams.
G. Deviation of the F voltage from its initial value. Obtained using a zero-shift circuit (difference amplifier). As the last step of the calibration process, potentiometer 13 is adjusted to give a displayed value (G) of zero units. Thereafter, G is proportional to the analyte concentration.

Note: The term "relative optical power" above refers to the optical power as measured with the particular detection system used in this application. Generally, the sensitivity of the detection system will not be the same at the two different wavelengths, and, in reality, the "relative optical powers" are not absolutely equal at the point C. They produce, however, equal responses in the detection circuit of this system. The fact that the powers are not absolutely equal has no significance to the operation of the system of this invention.

Referring back to FIG. 1, the output beams "A" and "B" of the lasers are combined in the beam combiner 3. The combined beam "C" is directed into a sample 4, such as an ear lobe. After reflection or transmission, the optical power is as shown at curve "D".

The optical system includes collimating means 32 and 34, respectively, i.e., lenses or mirrors to direct the sample channel beam "C" into the sample 4 and from the sample 4 beam "D" to the sample channel detectors 5.

The system uses a photoconductive PbS infrared detector 5 operating at room temperature. Its spectral sensitivity peaks at about 2.0 to 2.5 μm. The PbS detector 5 is operated in the classical bolometer circuit, and AC-coupled to a preamplifier 6. Other detectors sensitive in the relevant wavelength range could be used, with the appropriate coupling and amplifying method.

The output of the PbS detector 5 is quantified using a lock-in amplifier 7 that uses the signal produced by a square wave generator 10 as its reference signal. The output "E" of the lock-in amplifier 7 is a rectified direct-current signal proportional to the alternating-current signal produced by the detector 5. It is important to preserve the sign (phase) of the AC signal, because these signals are used for closed-loop control. For this reason, simple rectification where the phase is lost cannot be used. The present circuitry takes care of this phase selection requirement. The error signal "E" from lock-in amplifier 7 is integrated over time in integrator 8 to produce a control signal "F".

The operation of the system is governed by the square wave generator 10 operating at a frequency of typically between 10 Hz and 100 kHz, and using the techniques of this example, 1 Khz. The generator 10 signal determines which one of the two wavelengths and which one of the two corresponding intensity levels is to be used at any given moment.

It is assumed that the output of the lasers 1 and 2 are proportional to intensity control voltages (if the control voltage is zero, then the laser beam is off). If in a particular embodiment the lasers should be of a type whose intensity cannot be controlled by a voltage, then an appropriate modulator is used to the same effect. The inverter 11 ensures that the lasers operate in antiphase, or that one of them is "off" while the other is "on". The analog multiplier 9 changes the intensity of the beam between the two intensity values and adjusts one of the intensities according to the output of the integrator 8. As long as that output is non-zero, the intensity is constantly adjusted to zero the output of laser 2.

During operation, the error signal servoes itself to zero. This establishes the basic equisensitivity of the channels at the wavelengths initially selected. The intensity control signal from integrator 8 is also used as the basis for the glucose concentration display. The zero point of this signal is set by comparison with a reference voltage $V_R$ in the difference amplifier 12 established by DC reference voltage $V_o$ across precision potentiometer 13. The resulting voltage "G" is scaled and displayed in the display unit 14 to show the glucose concentration.

D. AUTOMATIC WAVELENGTH TUNING

An automatic calibration system option is shown in dotted lines in FIG. 1 as part of the present invention. The reference wavelength selected for measurement depends on the calibration of the subject to be tested. The calibration and the subsequent measurements are performed at a well-defined and easily available test site 4, such as the ear lobe or the skin of the fingerwebs, where the glucose concentration in blood is known. This glucose in blood concentration should preferably be low. To perform the calibration, the switch 15 is closed and the sample 4 is moved In and Out of the beam, or the beam is moved In and Out of the sample, by actuator 16 and beamshifter mechanism 17 at a low frequency, for instance 1 Hz. The intensity control signal, that is to say, the output of the integrator 8, will vary at the same frequency. If the matrix extinction of the sample 4 is not exactly the same at the two wavelengths, the amplitude of this variation is obtained at the output of lock-in amplifier 18, using the timing signal of the actuator 16 on line 36 as the reference. A wavelength control signal $\Delta V$ is obtained by integrating the output of the lock-in amplifier 18 in the integrator 19. It is assumed that the laser 1 can be tuned using a control voltage.

The exact reference wavelength obtained is noted and kept on record in a digital memory or computer 20 for that particular patient.

Potentiometer 13 is used to set the display to show a concentration value equal to the known concentration (zero or non-zero) of the calibration sample. The sensitivity of the intensity control signal to glucose concentration, known on the basis of previous tests and substantially constant at constant path length in the sample, is used to establish the complete response function of the system.

The measurement must always be done exactly at the same test site for a particular patient in order to preserve the validity of the calibration. To that effect, an optical device, interfacing with the basic optical system, may be semi-permanently attached to the test subject at a suitable test site. This is depicted schematically in FIG. 3. The optical device may, for example, take the appearance of an earring 24, having an optical input element 22 on one side of the ear lobe 4 and an optical output element 23 on the other side of the ear lobe, both transparent at the measurement wavelengths. The device 24 has the property of maintaining the probe at a fixed position on the ear lobe.

In a living test subject, the dependence of the signal on path length may cause the pulsing of the blood circulation to be seen, depending on the measuring geometry. This can be used to select the exact moment of recording the signal to occur at a constant phase of the pulse.

The pulsing effect is only seen on the signal if the system is fast enough. This will require the wavelength-alternating frequency to be preferably at least of the order of 1 kHz, and the servo loop cutoff frequency (essentially the lock-in cutoff frequency or the inverse of the output time constant divided by $2\pi$) at least of the order of 10 Hz. The system can also be deliberately made slow so that the pulsing is not seen and does not affect the accuracy.

Accordingly, an optional provision, shown by dotted line 50, is provided in FIG. 1, wherein an analog computing circuit or, preferably, a digital computer 21, may be used to control the taking of the reading at a constant phase of the pulse cycle, be it at the systolic or diastolic extremes or somewhere else, and coupling this control signal back to one of the lasers for intensity control. It is not important which phase is used, as long as it is always the same.

EQUIVALENTS

Those skilled in the art will know, or be able to ascertain using no more than routine experimentation, many equivalents to the specific embodiments of the invention described herein. For example, it may be possible to produce more than one wavelength from a given laser, so that switching between two widely spaced wavelengths of one laser may be used in place of the two laser sources 1 and 2. Light sources, other than lasers, may be used and filtered to produce monochromatic light.

These and all other equivalents are intended to be encompassed by the following claims.

We claim:

1. A method for non-invasive in vivo determining and measuring in a living body matrix the concentration of an analyte which absorbs electromagnetic radiation of wavelength $\lambda_1$, this method comprising the steps of:

a) generating said radiation of wavelength $\lambda_1$ and another wavelength of electromagnetic radiation $\lambda_2$ at which the absorption coefficient of the analyte is different from the one at $\lambda_1$, and wherein the extinction coefficient of the matrix is the same at $\lambda_1$ and at $\lambda_2$;

b) combining said radiations into a probing beam which alternates in time at wavelengths $\lambda_1$ and $\lambda_2$, the intensity of the beam being controllable in at least one of the wavelength durations, and directing this beam, from a location outside the body, at the body to produce an incident beam;

c) detecting the incident beam after it has traversed a path in the body and exited the body and producing an alternating signal corresponding to the difference between the intensities of the two wavelength radiations in the incident beam and wherein the alternating signal is nulled when substantially no analyte, or minimal analyte, is present in the sample;

d) generating an intensity control signal from the said alternating signal;

e) using the said intensity control signal to control the intensity of one of the two wavelength radiations of the probing beam to reduce the alternating signal substantially to zero;

f) using the value of the intensity control signal needed to restore the alternating signal substantially to zero as a measure of the concentration of the analyte in the matrix.

2. The method according to claim 1 wherein one of the wavelengths $\lambda_1$ and $\lambda_2$ is tuned by the steps of:

a) changing periodically the relation of a calibration sample to the probing beam at a frequency substantially lower than the wavelength frequency, so that the sample is alternately in and out or the beam;

b) generating a wavelength control signal by rectifying the alternating component of the intensity control signal; and c) using the wavelength control signal to tune the wavelength of one of the radiations to reduce the alternating component of the intensity control signal substantially to zero.

3. The method according to claim 1, where the matrix exhibits pulsatile variations of thickness or composition, and the instantaneous value of the intensity control signal is recorded at a constant phase of the pulsatile cycle.

4. The method according to claim 1 wherein the analyte is glucose and the matrix is the human body.

5. Measurement apparatus for non-invasive in vivo determination of an unknown concentration of an analyte that absorb electromagnetic radiation and is dissolved or dispersed in a living body matrix sample, comprising:

a) generating means external to the body matrix for generating a probe beam of the said radiation which contains, alternating in time, two different and substantially monochromatic wavelengths such that, at the two wavelengths, the extinction caused by the combined effects of absorption and scattering in the matrix is equal, but the absorption produced by the analyte is different at one wavelength;

b) optical means external to the body matrix for transmitting this beam into the body matrix;

c) collecting means for collecting the beam after it is has traversed at least a portion of the body matrix and exited the body matrix, said collecting means comprising a detector sensitive to both said wavelengths and providing in response an alternating-current signal;

d) electronic means to rectify and integrate the alternating current signal from the detector at the wavelength-alternating frequency to produce an intensity control signal;

e) control means for controlling the intensity of one of the wavelengths using the said intensity control signal so that the alternating-current signal from the detector is initially maintained substantially at zero with no analyte present in the body matrix and when analyte is present using the intensity control signal to force the alternating-current signal back to substantially zero; and f) conditioning and display means to condition and display the value of the control signal required to maintain the signal from the detector substantially at zero in the presence of analyte.

6. Apparatus according to claim 5, in which the analyte is glucose to be measured in human or animal body tissue, the two different wavelengths being between about 1 to 2.5 μm.

7. A non-invasive measurement system for determining in vivo the concentration of an analyte in an absorbing matrix of a living body comprising:

a) generating means external to the body for generating a beam of radiation at said matrix, said beam comprising pulses of energy at different wavelengths $\lambda_1$ and $\lambda_2$ wherein $\lambda_1$ is highly absorbed by said analyte and $\lambda_2$ is substantially non-absorbed by said analyte and the extinction coefficient of the matrix is the same at $\lambda_1$ and $\lambda_2$;

b) detector means external to the body for detecting the intensity of the beam after it has been subjected to said analyte and exited the body and generating an electrical signal which is substantially zero when minimum analyte is present in the matrix;

c) processing means external to the body for processing the electrical signal to form a control signal;

d) control means external to the body responsive to said control signal for adjusting the intensity of one of said energy pulses in accordance with said control signal to maintain said electrical signal at zero.

8. The system of claim 7 wherein the generating means comprises pulsed laser sources, one of which emits energy at $\lambda_1$, the other at $\lambda_2$ and wherein said sources are energized and de-energized, such that when one source is energized, the other is de-energized and vice versa.

9. The system of claim 8, including a reference signal, and wherein the control signal is compared with the reference signal and display means wherein the difference between the compared signals is displayed as a measure of the concentration of said analyte.

10. The system of claim 9 wherein the analyte is glucose and the absorbing matrix is the human body.

11. A method for non-invasive determining and measuring in a living body matrix the concentration of an analyte which absorbs electromagnetic radiation of wavelength $\lambda_1$, this method comprising the steps of:

a) generating said radiation of wavelength $\lambda_1$ and another wavelength of electromagnetic radiation $\lambda_2$ at which the absorption coefficient of the analyte is different from the one at $\lambda_1$, and wherein the extinction coefficient of the matrix is the same as $\lambda_1$ and at $\lambda_2$;

b) combining said radiations into a probing beam with alternate half-periods at $\lambda_1$ and $\lambda_2$, the intensity of the beam being controllable in at least one of the half-periods, and directing this beam at the matrix from a location external to the matrix;

c) detecting the beam after it has traversed a path in the matrix and exited the matrix to produce an alternating-current signal corresponding to the alternation of the two wavelength radiations in the incident beam which alternating current signal is substantially nulled when the concentration of analyte in the matrix is nulled;

d) generating an intensity control signal from the said alternating-current signal;

e) using the said intensity control signal to control the intensity ratio of the two wavelength radiations of the probing beam to maintain the ratio at unity and thereby maintain the alternating-current signal substantially at zero;

f) using the intensity control signal as a measure of the concentration of the analyte in the matrix.

12. The method according to claim 11 wherein one of the wavelengths $\lambda_1$ and $\lambda_2$ is tuned by the steps of:

a) changing periodically the relation of a calibration sample to the measuring beam at a frequency substantially lower than the wavelength alternating frequency, so that the sample is alternately in and out of the beam;

b) generating a wavelength control signal by rectifying the alternating component of the intensity control signal;

c) using the wavelength control signal to tune the wavelength of one of the lasers so as to reduce the alternating component of the intensity control signal substantially to zero.

13. The method according to claim 11, where the matrix exhibits pulsatile variations of thickness or composition, and the instantaneous value of the intensity control signal is recorded at a constant phase of the pulsatile cycle.

14. A measurement system for non-invasively determining the concentration of glucose in an absorbing matrix of a living body comprising:

a) generating means external to the body for generating a beam of light at said matrix, said beam comprising light pulses of energy at different wavelengths $\lambda_1$ and $\lambda_2$ wherein $\lambda_1$ is highly absorbed by glucose and $\lambda_2$ is substantially non-absorbed by glucose and wherein the extinction coefficient of the matrix is the same at $\lambda_1$ and $\lambda_2$;

b) detector means external to the body for detecting the intensity of the beam after it has been subjected to glucose in the matrix and has exited the matrix and generating an electrical signal proportional to the ratio of the intensities of the radiation at the two different wavelengths, which ratio is pre-set to unit with minimum glucose in the matrix;

c) process means external to the body for processing the electrical signal to form a control signal;

d) control means external to the body responsive to said control signal for adjusting the intensity of one of said energy pulses in accordance with said control signal to maintain the ratio of the intensities at unity and thereby force the electrical signal to zero.

15. The system of claim 14 wherein the generating means comprises pulsed laser sources, one of which emits energy at $\lambda_1$, the other at $\lambda_2$ and wherein said sources are energized and de-energized, such that when one source is energized, the other is de-energized and vice versa.

16. The system of claim 15, including a reference signal, and wherein the control signal is compared with the reference signal and display means wherein the difference between the compared signals is displayed as a measure of the concentration of said glucose.

17. A method for determining and measuring in a sample matrix the concentration of an analyte which absorbs electromagnetic radiation of wavelength $\lambda_1$, this method comprising the steps of:
   a) generating said radiation of wavelength $\lambda_1$ and another wavelength of electromagnetic radiation $\lambda_2$ at which the absorption coefficient of the analyte is different from the one at $\lambda_1$, and wherein the extinction coefficient of the matrix is the same at $\lambda_1$ and at $\lambda_2$;
   b) combining said radiations into a probing beam which alternates in time at wavelengths $\lambda_1$ and $\lambda_2$, the intensity of the beam being controllable in at least one of the wavelength durations, and directing this beam at the sample to produce an incident beam;
   c) detecting the incident beam after it has traversed a path in the sample and producing an alternating signal corresponding to the difference between the intensities of the two wavelength radiations in the incident beam and wherein the alternating signal is nulled when substantially no analyte, or minimal analyte, is present in the sample;
   d) generating an intensity control signal from the said alternating signal;
   e) using the said intensity control signal to control the intensity of one of the two wavelength radiations of the probing beam to reduce the alternating signal substantially to zero;
   f) using the value of the intensity control signal needed to restore the alternating signal substantially to zero as a measure of the concentration of the analyte in the matrix; and
   g) tuning the wavelengths of one of the radiations by the steps of:
      (i) changing periodically the relation of a calibration sample to the probing beam at a frequency substantially lower than the wavelength frequency, so that the sample is alternately in and out of the beam;
      (ii) generating a wavelength control signal by rectifying the alternating component of the intensity control signal; and
      (iii) using the wavelength control signal to tune the wavelength of one of the radiations to reduce the alternating component of the intensity control signal substantially to zero.

18. A method for determining and measuring in a sample matrix the concentration of an analyte which absorbs electromagnetic radiation of wavelength $\lambda_1$, this method comprising the steps of:
   a) generating said radiation of wavelength $\lambda_1$ and another wavelength of electromagnetic radiation $\lambda_2$ at which the absorption coefficient of the analyte is different from the one at $\lambda_1$, and wherein the extinction coefficient of the matrix is the same at $\lambda_1$ and at $\lambda_2$;
   b) combining said radiations into a probing beam with alternate half-periods at $\lambda_1$ and $\lambda_2$, the intensity of the beam being controllable in at least one of the half-periods, and directing this beam at the sample;
   c) detecting the beam after it has traversed a path in the sample to produce an alternating-current signal corresponding to the alternation of the two wavelength radiations in the incident beam which alternating current signal is substantially nulled when the concentration of analyte in the matrix is nulled;
   d) generating an intensity control signal from the said alternating-current signal;
   e) using the said intensity control signal to control the intensity ratio of the two wavelength radiations of the probing beam to maintain the ratio at unity and thereby maintain the alternating-current signal substantially at zero;
   f) using the intensity control signal as a measure of the concentration of the analyte in the matrix; and
   g) tuning one of the wavelengths $\lambda_1$ and $\lambda_2$ by the steps of:
      (i) changing periodically the relation of a calibration sample to the measuring beam at a frequency substantially lower than the wavelength alternating frequency, so that the sample is alternately in and out of the beam;
      (ii) generating a wavelength control signed by rectifying the alternating component of the intensity control signal;
      (iii) using the wavelength control signal to tune the wavelength of one of the radiations so as to reduce the alternating component of the intensity control signal substantially to zero.

* * * * *

UNITED STATES PATENT AND TRADEMARK OFFICE
CERTIFICATE OF CORRECTION

PATENT NO. : 5,112,124
DATED : May 12, 1992
INVENTOR(S) : Hannu Harjunmaa, Robert A. Peura and Yitzhak Mendelson It is certified that error appears in the above-identified patent and that said Letters Patent is hereby corrected as shown below:

Col. 10, line 57, delete "unit" and insert ---unity---.

Signed and Sealed this

Seventh Day of December, 1993

Attest:

BRUCE LEHMAN

Attesting Officer

Commissioner of Patents and Trademarks